(12) United States Patent
Call

(10) Patent No.: US 8,173,431 B1
(45) Date of Patent: *May 8, 2012

(54) MAIL SCREENING TO DETECT MAIL CONTAMINATED WITH BIOLOGICAL HARMFUL SUBSTANCES

(75) Inventor: Charles J. Call, Albuquerque, NM (US)

(73) Assignee: FLIR Systems, Inc., Wilsonville, OR (US)

( * ) Notice: Subject to any disclaimer, the term of this patent is extended or adjusted under 35 U.S.C. 154(b) by 1490 days.

This patent is subject to a terminal disclaimer.

(21) Appl. No.: 11/558,269

(22) Filed: Nov. 9, 2006

Related U.S. Application Data

(63) Continuation-in-part of application No. 11/058,442, filed on Feb. 15, 2005, now abandoned, which is a continuation-in-part of application No. 10/066,404, filed on Feb. 1, 2002, now Pat. No. 6,887,710, which is a continuation-in-part of application No. 09/775,872, filed on Feb. 1, 2001, now Pat. No. 6,729,196, which is a continuation-in-part of application No. 09/265,619, filed on Mar. 10, 1999, now Pat. No. 6,267,016, and a continuation-in-part of application No. 09/265,620, filed on Mar. 10, 1999, now Pat. No. 6,363,800, said application No. 10/066,404 and a continuation-in-part of application No. 09/955,481, filed on Sep. 17, 2001, now Pat. No. 6,695,146, and a continuation-in-part of application No. 09/494,962, filed on Jan. 31, 2000, now Pat. No. 6,290,065, is a continuation-in-part of application No. 09/191,980, filed on Nov. 13, 1998, now Pat. No. 6,062,392.

(60) Provisional application No. 60/337,674, filed on Nov. 13, 2001.

(51) Int. Cl.
  *G01M 3/02* (2006.01)
  *G01N 33/00* (2006.01)
  *G01N 1/14* (2006.01)

(52) U.S. Cl. .......... 436/53; 436/104; 436/106; 436/110; 436/174; 422/88; 422/83; 73/23.2

(58) Field of Classification Search ............... 436/53, 436/104, 106, 110, 174; 422/83, 88; 73/23.2
See application file for complete search history.

(56) References Cited

U.S. PATENT DOCUMENTS
877,460 A    1/1908   Brunner et al.
(Continued)

FOREIGN PATENT DOCUMENTS
WO    WO 03/089907    10/2003
(Continued)

OTHER PUBLICATIONS

Giechaskiel et al., "A metric for health effects studies of diesel exhaust particles," *Aerosol Science* vol. 40: 639-651, 2009.

(Continued)

*Primary Examiner* — Lyle Alexander
(74) *Attorney, Agent, or Firm* — McAfee & Taft

(57) ABSTRACT

A multi-tier approach for use in a mailroom for detecting bio-threats conveyed by mail. In a first tier procedure, mail entering the mailroom is continuously automatically screened at a mail screening station to detect a potential bio-threat contamination. If a potential bio-threat is detected, an alarm signal is generated, a sample of the potential bio-threat is collected, and a second tier procedure is initiated. The second tier procedure uses a manual test, such as a nucleic acid amplification and detection assay to detect any of a plurality of different specific bio-threats in the sample. If a specific bio-threat is found, appropriate steps are taken to limit spread of the bio-threat and exposure of personnel. A third tier procedure uses a manual assay to check for a specific toxin in background samples collected over a predefined time interval at each mail screening station and in the air handling system for the mailroom.

13 Claims, 4 Drawing Sheets

U.S. PATENT DOCUMENTS

| | | | |
|---|---|---|---|
| 902,958 A | 11/1908 | Galusha | |
| 906,038 A | 12/1908 | Lauder | |
| 1,603,878 A | 10/1926 | Smith | |
| 1,662,870 A | 3/1928 | Stancliffe | |
| 1,749,920 A | 3/1930 | Modave | |
| 1,807,378 A | 5/1931 | Budil | |
| 1,825,274 A | 9/1931 | Leach | |
| 2,937,780 A | 5/1960 | Beckwith | 220/560.14 |
| 2,939,545 A | 6/1960 | Silverman | |
| 3,001,914 A | 9/1961 | Andersen | 435/30 |
| 3,469,934 A | 9/1969 | Bocard et al. | |
| 3,518,815 A | 7/1970 | McFarland et al. | 73/863.22 |
| 3,572,128 A | 3/1971 | Hemeon | 73/863.24 |
| 3,633,405 A | 1/1972 | Noll | 73/28.06 |
| 3,693,457 A | 9/1972 | Pilat | 73/432 |
| 3,754,868 A | 8/1973 | Witz et al. | 23/254 |
| 3,760,630 A | 9/1973 | Brumbaugh | 73/28.05 |
| 3,891,550 A | 6/1975 | Gray et al. | 210/67 |
| 3,901,798 A | 8/1975 | Peterson | 209/143 |
| 3,922,905 A | 12/1975 | Roth | 73/28.04 |
| 3,932,151 A | 1/1976 | Lau | 55/229 |
| 3,942,357 A | 3/1976 | Jenkins | 73/31.07 |
| 3,970,428 A | 7/1976 | Barringer | 23/230 |
| 3,972,226 A | 8/1976 | Rountree et al. | 73/28.05 |
| 3,983,743 A | 10/1976 | Olin et al. | 73/28 |
| 3,997,297 A | 12/1976 | Jenkins et al. | 436/153 |
| 4,111,049 A | 9/1978 | Lerner et al. | 73/864.73 |
| 4,133,202 A | 1/1979 | Marple | 73/28 |
| 4,301,002 A | 11/1981 | Loo | 209/143 |
| 4,321,822 A | 3/1982 | Marple et al. | 73/28 |
| 4,350,571 A | 9/1982 | Erickson | 203/21 |
| 4,387,603 A | 6/1983 | Nelson | 73/863.22 |
| 4,415,265 A | 11/1983 | Campillo et al. | 356/338 |
| 4,452,068 A | 6/1984 | Loo | 73/28 |
| 4,473,384 A | 9/1984 | Lefkowitz | 55/290 |
| 4,580,440 A * | 4/1986 | Reid et al. | 73/31.07 |
| 4,590,792 A | 5/1986 | Chiang | 73/28 |
| 4,640,140 A | 2/1987 | Burghoffer et al. | 73/863.22 |
| 4,670,135 A | 6/1987 | Marple et al. | 209/143 |
| 4,689,052 A | 8/1987 | Ogren et al. | 55/17 |
| 4,697,462 A | 10/1987 | Daube, Jr. et al. | 73/863.21 |
| 4,742,009 A | 5/1988 | Beverly et al. | 436/57 |
| 4,764,186 A | 8/1988 | Langer | 95/268 |
| 4,767,524 A | 8/1988 | Yeh et al. | 209/143 |
| 4,790,860 A | 12/1988 | Sexton | 55/59 |
| 4,820,920 A | 4/1989 | Bather | 250/282 |
| 4,872,972 A | 10/1989 | Wakabayashi et al. | 209/143 |
| 4,877,430 A | 10/1989 | Gutermuth | 55/269 |
| 4,877,516 A | 10/1989 | Schram | 209/155 |
| 4,941,899 A | 7/1990 | Liu | 73/863.23 |
| 4,942,297 A | 7/1990 | Johnson et al. | 250/304 |
| 4,961,966 A | 10/1990 | Stevens et al. | 427/299 |
| 4,972,957 A | 11/1990 | Liu et al. | 209/143 |
| 4,987,286 A | 1/1991 | Allen | 219/121.68 |
| 4,990,740 A | 2/1991 | Meyer | 219/121.52 |
| 5,039,490 A | 8/1991 | Marsoner et al. | 422/82.01 |
| 5,040,424 A | 8/1991 | Marple et al. | 73/863.23 |
| 5,063,164 A | 11/1991 | Goldstein | 436/169 |
| 5,128,539 A | 7/1992 | Rodgers et al. | 250/255 |
| 5,144,175 A | 9/1992 | Craggs | 310/63 |
| 5,162,810 A | 11/1992 | Onisawa et al. | 343/912 |
| 5,201,231 A | 4/1993 | Smith | 73/863.22 |
| 5,254,861 A | 10/1993 | Carpenter et al. | 250/573 |
| 5,294,410 A | 3/1994 | White | 422/171 |
| 5,299,141 A | 3/1994 | Hungerford et al. | 702/49 |
| 5,304,125 A | 4/1994 | Leith | 604/57 |
| 5,318,609 A | 6/1994 | Kittler | 55/443 |
| 5,326,537 A | 7/1994 | Cleary | 422/173 |
| 5,332,550 A | 7/1994 | Booker | 422/83 |
| 5,412,975 A | 5/1995 | Raabe et al. | 73/28.04 |
| 5,421,214 A | 6/1995 | Burgdorfer | 73/863.22 |
| 5,425,263 A | 6/1995 | Davies et al. | 73/28.05 |
| 5,425,802 A | 6/1995 | Burton et al. | 95/32 |
| 5,428,222 A | 6/1995 | Alexay | 250/343 |
| 5,437,198 A | 8/1995 | John | 73/863.22 |
| 5,461,473 A | 10/1995 | Pratt et al. | 356/141.3 |
| 5,472,645 A | 12/1995 | Rock et al. | 261/79.1 |
| 5,498,271 A | 3/1996 | Marple et al. | 55/321 |
| 5,512,216 A | 4/1996 | Rock et al. | 261/79.1 |
| 5,518,697 A | 5/1996 | Dalla Betta et al. | 422/173 |
| 5,533,406 A | 7/1996 | Geise | 73/863.22 |
| 5,534,328 A | 7/1996 | Ashmead | 428/166 |
| 5,552,051 A | 9/1996 | Wang et al. | 210/604 |
| 5,553,795 A | 9/1996 | Tsai et al. | 241/40 |
| 5,584,557 A | 12/1996 | Alexay | 362/32 |
| 5,585,575 A * | 12/1996 | Corrigan et al. | 73/863.71 |
| 5,658,537 A | 8/1997 | Dugan | 422/191 |
| 5,669,811 A | 9/1997 | Zaniewski | 454/16 |
| 5,681,752 A | 10/1997 | Prather | 436/173 |
| 5,693,895 A | 12/1997 | Baxter | 73/863.22 |
| 5,760,314 A | 6/1998 | Bromberg et al. | 73/863.21 |
| 5,776,754 A | 7/1998 | Caldwell | 435/325 |
| 5,786,894 A | 7/1998 | Shields et al. | 356/338 |
| 5,788,741 A | 8/1998 | Burton et al. | 95/32 |
| 5,811,062 A | 9/1998 | Wegeng et al. | 422/129 |
| 5,858,043 A | 1/1999 | Geise | 55/462 |
| 5,859,375 A | 1/1999 | Danylewych-May et al. | 73/864.71 |
| 5,914,091 A | 6/1999 | Holst et al. | 422/173 |
| 5,925,960 A | 7/1999 | Hayes | 310/211 |
| 5,932,795 A | 8/1999 | Koutrakis et al. | 73/28.01 |
| 5,935,339 A | 8/1999 | Henderson et al. | 134/1 |
| 5,942,699 A | 8/1999 | Ornath et al. | 73/863.21 |
| 5,949,001 A | 9/1999 | Willeke | 73/865.5 |
| 5,967,332 A | 10/1999 | Willeke | 209/132 |
| 5,997,619 A | 12/1999 | Knuth et al. | 96/224 |
| 6,001,145 A | 12/1999 | Hammes | 55/471 |
| RE36,489 E | 1/2000 | Alexay | 250/343 |
| 6,024,923 A | 2/2000 | Melendez et al. | 422/82.08 |
| 6,036,027 A | 3/2000 | Grimes | 209/725 |
| 6,062,392 A | 5/2000 | Birmingham et al. | 209/143 |
| 6,070,658 A | 6/2000 | Cipriani | 165/166 |
| 6,082,439 A | 7/2000 | Kato et al. | 165/79 |
| 6,082,445 A | 7/2000 | Dugan | 165/167 |
| 6,101,886 A | 8/2000 | Brenizer et al. | 73/863.23 |
| 6,110,247 A | 8/2000 | Birmingham et al. | 55/442 |
| 6,125,845 A | 10/2000 | Halvorsen et al. | 128/200.24 |
| 6,193,587 B1 | 2/2001 | Lin et al. | 451/56 |
| 6,194,731 B1 | 2/2001 | Jeys et al. | 250/461.2 |
| 6,217,636 B1 | 4/2001 | McFarland | 95/216 |
| 6,235,002 B1 | 5/2001 | Carver, Jr. et al. | 604/183 |
| 6,240,768 B1 | 6/2001 | Lemmonier | 73/28.05 |
| 6,267,016 B1 | 7/2001 | Call et al. | 73/863.22 |
| 6,284,025 B1 | 9/2001 | Kreisberg et al. | 95/267 |
| 6,293,861 B1 | 9/2001 | Berry | 454/255 |
| 6,324,927 B1 | 12/2001 | Ornath et al. | 73/864.33 |
| 6,334,365 B1 | 1/2002 | Linker et al. | 73/864.81 |
| 6,363,800 B1 | 4/2002 | Call et al. | 73/863.22 |
| 6,370,406 B1 | 4/2002 | Wach et al. | 600/310 |
| 6,386,015 B1 | 5/2002 | Rader et al. | 73/31.05 |
| 6,392,313 B1 | 5/2002 | Epstein et al. | 290/52 |
| 6,435,043 B1 | 8/2002 | Ferguson et al. | 73/863.22 |
| 6,443,314 B2 | 9/2002 | Shiraiwa et al. | 210/474 |
| 6,488,900 B1 | 12/2002 | Call et al. | 422/173 |
| 6,511,854 B1 | 1/2003 | Asanov et al. | 436/518 |
| 6,532,067 B1 | 3/2003 | Chang et al. | 356/318 |
| 6,532,835 B1 | 3/2003 | Saaski et al. | 73/863.21 |
| 6,573,836 B1 | 6/2003 | Gitis et al. | 340/603 |
| 6,610,977 B2 | 8/2003 | Megerle | 250/287 |
| 6,639,733 B2 | 10/2003 | Minano et al. | 359/728 |
| 6,695,146 B2 | 2/2004 | Call et al. | 209/143 |
| 6,707,539 B2 | 3/2004 | Selinfreund et al. | 356/71 |
| 6,729,196 B2 | 5/2004 | Moler et al. | 73/863.22 |
| 6,805,751 B2 | 10/2004 | Allen | 134/1 |
| 6,826,422 B1 | 11/2004 | Modell et al. | 600/407 |
| 6,829,919 B2 | 12/2004 | Sioutas et al. | 73/865.5 |
| 6,834,533 B2 | 12/2004 | Megerle | 73/45.4 |
| 6,885,440 B2 | 4/2005 | Silcott et al. | 356/73 |
| 6,887,710 B2 | 5/2005 | Call et al. | 436/53 |
| 6,908,567 B2 | 6/2005 | Uziel | 216/66 |
| 6,949,147 B2 | 9/2005 | Uziel et al. | 134/1 |
| 6,984,524 B2 | 1/2006 | Nguyen et al. | 436/172 |
| 7,091,870 B2 | 8/2006 | Tsutsumi et al. | 340/632 |
| 7,096,125 B2 | 8/2006 | Padmanabhan et al. | 702/24 |
| 7,106,442 B2 | 9/2006 | Silcott et al. | 356/338 |
| 7,113,277 B2 | 9/2006 | Craig | 356/318 |
| 7,173,257 B1 | 2/2007 | Warrick et al. | 250/458.1 |

| | | | |
|---|---|---|---|
| 7,205,152 B2* | 4/2007 | Swider | 436/1 |
| 7,261,008 B2 | 8/2007 | Saaski et al. | 73/863.22 |
| 7,265,669 B2 | 9/2007 | Call et al. | 340/539.26 |
| 7,304,259 B2* | 12/2007 | Schwarz et al. | 209/584 |
| 7,578,973 B2 | 8/2009 | Call et al. | 422/83 |
| 7,591,980 B2 | 9/2009 | Call et al. | 422/91 |
| 7,720,567 B2 | 5/2010 | Doke et al. | 700/117 |
| 7,799,567 B1 | 9/2010 | Call | 436/53 |
| 2001/0047136 A1 | 11/2001 | Domanik et al. | 600/473 |
| 2004/0028561 A1 | 2/2004 | Daugherty et al. | 422/99 |
| 2004/0063197 A1 | 4/2004 | Tilles et al. | 435/287.2 |
| 2004/0104342 A1 | 6/2004 | Yamada et al. | 250/288 |
| 2004/0124366 A1 | 7/2004 | Zeng et al. | 600/473 |
| 2005/0070025 A1 | 3/2005 | Mooradian et al. | 250/461.1 |
| 2006/0030790 A1 | 2/2006 | Braig et al. | 600/584 |
| 2006/0257853 A1 | 11/2006 | Herman | 435/6 |
| 2008/0281528 A1 | 11/2008 | Relle, Jr. | 702/19 |

FOREIGN PATENT DOCUMENTS

| | | |
|---|---|---|
| WO | WO 2003/089661 | 10/2003 |
| WO | WO 2007/123349 | 11/2007 |

OTHER PUBLICATIONS

Jensen et al., "Sampling and Characteristics of Bioaerosols." *NIOSH: Manual of Analytical Methods*: 82-112, Jan. 15, 1998.

Kunzli et al., "Public health impact of outdoor and traffic-related air pollution: a European assessment," *Lancet* vol. 356: 795-801, 2000.

Lee et al., "Development and application of personal respirable particulate samplers (PRPS)," *Atmospheric Environment* vol. 40: 212-224, 2006.

Noll et al., "Relationship between elemental carbon, total carbon, and diesel particulate matter in several undergrond metal/non-metal mines," *Environmental Science & Technology* vol. 41, No. 3: 710-716, 2007.

Noll et al., "Using laser absorption techniques to monitor diesel particulate matter exposure," *Smart Biomedical and Physiological Sensor Technology, Proceedings of SPIE* vol. 6759: 11pp., 2007.

Primmerman, Charles., "Detection of Biological Agents." *Lincoln Laboratory Journal*, vol. 12, No. 1: 3-32, 2000.

Wittmaack, Klaus., "In search of the most relevant parameter for quantifying lung inflammatory response to nanoparticle exposure: particle number, surface area, or what?" *Environmental Health Perspectives* vol. 115, No. 2: 187-194, 2007.

Environment Protection Agency (U.S.) "Health assessment document for diesel engine exhaust", EPA/600/8-90/057F: 669pp., May 2002.

\* cited by examiner

MAIL SCREENING TO DETECT MAIL CONTAMINATED WITH BIOLOGICAL HARMFUL SUBSTANCES

RELATED APPLICATIONS

This application is a continuation-in-part of prior copending U.S. patent application Ser. No. 11/058,442, filed on Feb. 15, 2005, which itself is a continuation-in-part of a prior U.S. patent application Ser. No. 10/066,404, filed on Feb. 1, 2002, which issued as U.S. Pat. No. 6,887,710 on May 3, 2005, and which itself is based on prior U.S. Provisional Patent Application Ser. No. 60/337,674, filed on Nov. 13, 2001, the benefits of the filing dates of which are hereby claimed under 35 U.S.C. §119(e) and 35 U.S.C. §120. U.S. patent application Ser. No. 10/066,404 is a continuation-in-part of prior U.S. patent application Ser. No. 09/775,872, filed on Feb. 1, 2001, which issued as U.S. Pat. No. 6,729,196 on May 4, 2004 and which is itself is a continuation-in-part of U.S. patent application Ser. No. 09/265,619, filed on Mar. 10, 1999, which issued as U.S. Pat. No. 6,267,016 on Jul. 31, 2001, and of prior U.S. patent application Ser. No. 09/265,620, filed on Mar. 10, 1999, which issued as U.S. Pat. No. 6,363,800 on Apr. 2, 2002, the benefit of the filing dates of which are hereby claimed under 35 U.S.C. §120. Further, U.S. patent application Ser. No. 10/066,404, is also a continuation-in-part of prior U.S. patent application Ser. No. 09/955,481, filed on Sep. 17, 2001, which issued as U.S. Pat. No. 6,695,146 on Feb. 24, 2004 and which itself is a continuation-in-part of prior U.S. patent application Ser. No. 09/191,980, filed on Nov. 13, 1998, which issued as U.S. Pat. No. 6,062,392 on May 16, 2000, and of U.S. patent application Ser. No. 09/494,962, filed on Jan. 31, 2000, which issued as U.S. Pat. No. 6,290,065 on Sep. 18, 2001, the benefit of the filing dates of which is hereby claimed under 35 U.S.C. §120.

BACKGROUND

After Sep. 11, 2001, letters contaminated with weapons-grade *Bacillus anthracis* (anthrax) spores passed through the United States Postal Service (USPS). Over 16 cases of documented infections and several deaths were directly attributed to such letters. By November 2001, over 32,000 individuals in the United States were taking antibiotics prescribed by physicians specifically as a prophylactic measure to combat a potential exposure to anthrax contaminated mail. Multiple mail processing facilities, and the equipment within those facilities, were contaminated by exposure to what appears to have been a statistically small number of intentionally contaminated letters.

In response to the threat posed by intentionally contaminated mail, most of the incoming mail passing through most of the larger USPS mail distribution centers is now screened for anthrax. However, not all mail handled by the USPS passes through one of these distribution centers. Furthermore, the USPS mail screening system only detects *Bacillus anthraces* (i.e., anthrax), but currently does not attempt to detect ricin, tularemia or any of the other biological hazardous threats or "bio-threats." Also, bulk mail such as boxes of pamphlets, and mass advertising mailings are not screened by the USPS and are often shipped by overnight carriers such as United Parcel Service (UPS), which does not screen any packages for bio-threats.

The USPS solution, which was developed by Northrop Grumman Corporation, uses a type of nucleic acid amplification and detection based on genetic fingerprinting known as polymerase chain reaction (PCR) technology. PCR uses polymerase enzymes to cause a chain reaction that results in a massive increase in the number of copies of a targeted gene sequence—but if and only if the targeted gene sequence is present in a sample being tested. For example, if a sample of paper dust extracted from an envelope in the mail does NOT contain the genes for anthrax, then the PCR test does not produce a positive result, since the gene is not present to be amplified by copying. On the other hand, if the paper dust sample contains multiple anthrax spores, the process will produce a readily detectable increase in the number of copies of the gene sequence. Thus, this detection technique normally provides a very dependable positive detection of the genes for anthrax. Other non-PCR nucleic acid amplification technologies could also be used.

In the USPS bio-threat detection scheme, samples are collected continuously, and an analysis of the samples is performed once per hour. In order to save money, the USPS decided it would only test for the anthrax genes, and not for other microbes or for the presence of other types of bio-threats such as ricin. The reasons for limiting the tests performed are understandable, since each test for each different type of harmful organism costs approximately $25-$30, and the Post Office has approximately 1300 sampling and PCR detection machines distributed throughout the United States. Each machine generates a new sample to be tested each hour, resulting in millions of tests per year and costs that will likely exceed $100 million/year. A relatively high continuing operating cost is thus one clear drawback to the USPS solution. Also, an initial capital equipment cost for the USPS sampling and detection system is on the order of $200,000 per system. For many smaller mail rooms, the initial cost of this system is thus also prohibitive.

The response time for the current USPS detection system is approximately two hours. Because of this relatively slow response time, the system only provides a "detect to treat" capability, since during the two hours before a positive detection of anthrax can occur, it can be assumed that the toxic agent will have spread throughout the mail facility. Clearly, it would be desirable to develop a system that is lower in cost to operate and which provides an immediate alert when a potential bio-threat is detected in the mail being screened. In addition, it would be desirable to screen the mail for other bio-threats besides anthrax.

SUMMARY

Accordingly, in consideration of the issues discussed above, an approach has been developed for screening mail that is passing through a mailroom, for contamination by a bio-threat, in a multi-tier approach. As used herein and in the claims that follow, the term "bio-threat" is intended to encompass a hazardous biological agent or bio-terror threat or bio-warfare threat, including any living organism (e.g., virus, bacteria, bacterial spore, or fungus) that is pathogenic (disease causing), and toxin that may be extracted from or produced by an organism (i.e., a plant, an animal, or fungus). In some embodiments, such threats are assumed to encompass biological particles of respirable size, that is, particles ranging from about 1 to about 10 microns.

An exemplary method for carrying out this approach begins with a first tier screening of the mail. During the first tier screen, the mail entering the mailroom is screened in batches to detect a potential bio-threat that may be conveyed by one or more pieces of the mail. If a potential bio-threat is detected during the first tier screening, the batch or a subset of the batch of mail that includes the one or more pieces of mail is isolated. Also, a sample of the potential bio-threat is collected, and a first tier alarm is produced, indicating that a potential bio-threat may have been detected. Next, a second tier screening of the sample collected during the first tier screening is carried out to attempt to identify a specific type of bio-threat comprising the sample. If it is confirmed by the second tier screening that the sample comprises a specific bio-threat, a series of predefined appropriate steps are initiated to limit contamination by preventing the specific bio-threat from spreading beyond the mailroom and to limit exposure of personnel to the specific bio-threat.

The method further includes the step of periodically carrying out a third tier screening to detect a potential bio-threat in at least one additional sample. This additional sample can either be a background sample collected over time from air circulated within the mailroom, or can be a background sample collected over time at a mail screening station through which mail passes while undergoing the first tier screening.

The step of continuously screening a batch of mail during the first tier screening can include the steps of collecting particles conveyed by the one or more pieces of mail from air passing over the batch of mail, and then irradiating the particles that are collected with light of a predefined waveband. A fluorescence signature of light emitted from the particles when thus irradiated is detected, and based upon the fluorescence signature, the method provides for automatically determining if the particles comprise a potential bio-threat. The step of continuously screening a batch of mail during the first tier can also include the steps of collecting the particles conveyed by the one or more pieces of mail from air passing over the batch of mail, and then impacting the particles onto a surface. The surface could be a solid surface, which allows for a bulk measurement of the fluorescence properties, or could be a gel which contains biological molecules, such as stains or dyes or labeled antibodies that bond with bio-threat particles. One or more biological molecules are selected a priori such that bio-threat particles become easily detected, for example, by fluorescence detection. The step of continuously screening the mail during the first tier can also include mixing a secondary aerosol with the particles conveyed by the one or more pieces of mail, such a secondary aerosol containing the biological molecules to be used to detect the bio-threats, such that the bio-threat particles become more easily detected.

The second tier screening can include performing a polymerase chain reaction (PCR) assay test of the sample that was collected during the first tier screening, wherein the PCR assay test is configured to identify at least one specific bio-threat. Alternatively, or in addition, the second tier screening can include the step of performing an immunoassay test on the sample that was collected during the first tier screening. The immunoassay test is selected to identify at least one specific bio-threat. The second tier screening may be split into two steps, wherein the first step is to perform a test that is different than the Tier 1 screening, so as to confirm that the possible bio-threat indeed has one additional characteristic of an actual bio-threat, and if positive, to then perform an analysis that attempts to identify the specific type of bio-threat comprising the sample. It should be recognized that PCR is but one of many different types of nucleic acid amplification and detection assays available, and as such PCR is intended to be exemplary, rather than limiting. Other available nucleic acid amplification and detection assays can also be employed.

The first tier screening can also include the steps of visually inspecting mail comprising parcels larger than letters, to detect any powder that may comprise a potential bio-threat. If a powder that may comprise a potential bio-threat is visually detected, a second tier screening of the powder is carried out to attempt to identify a specific bio-threat comprising the powder. If it is confirmed by the second tier screening that the sample comprises a specific bio-threat, the series of predefined appropriate steps are initiated to limit contamination by preventing the specific bio-threat from spreading beyond the mailroom and to limit exposure of personnel to the specific type of bio-threat.

The specific bio-threat can be spores, bacteria, viruses, micro-organisms, or toxins derived from biological organisms (including plants, animals, mold, and fungi.

Another aspect of the approach discussed herein is directed to an exemplary system configured for use in a mailroom, for screening mail that is passing through the mailroom, to detect contamination by a bio-threat, in a multi-tier approach. The exemplary system uses components that carry out functions generally as described in regard to the exemplary method discussed above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 2:
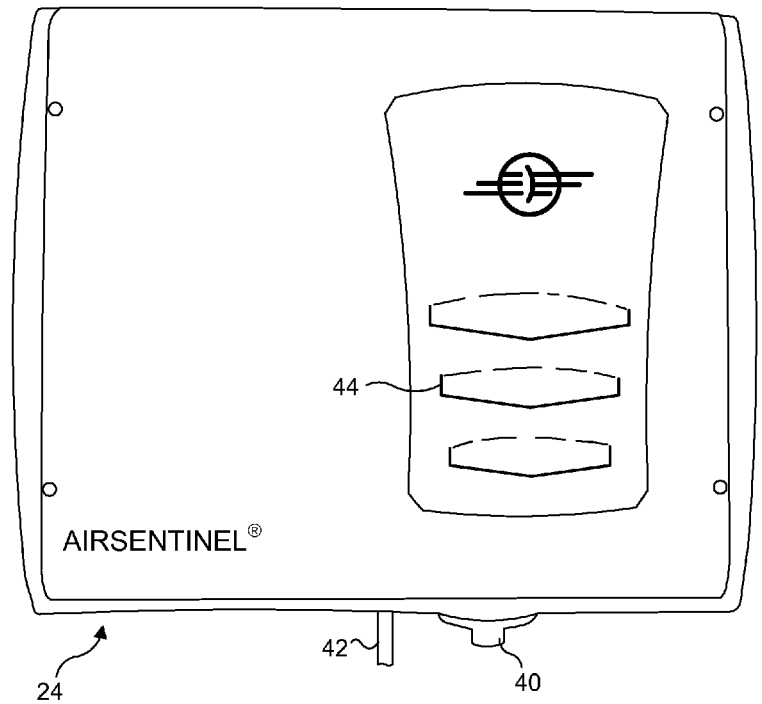
FIG. 2 is an elevational view of an exemplary automatic air sampler device for detecting bio-threats in real time.
Figure 3:
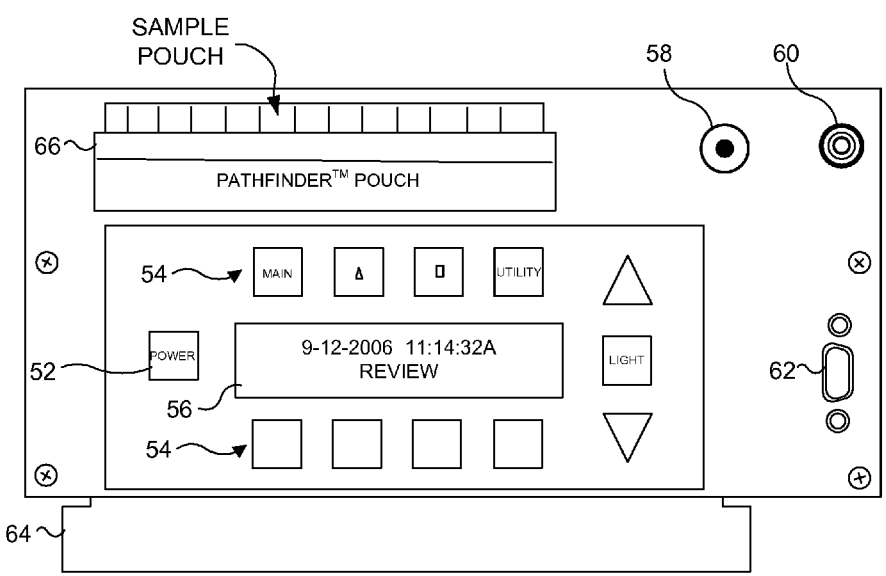
Figure 4:
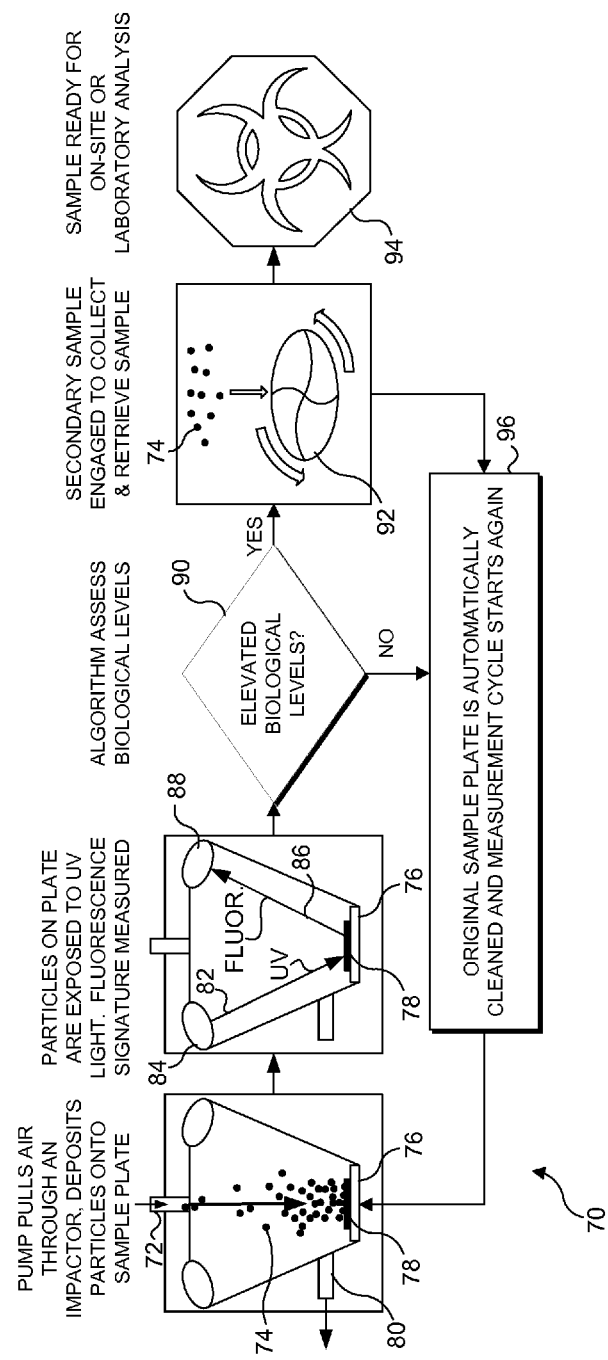
Figure 5:
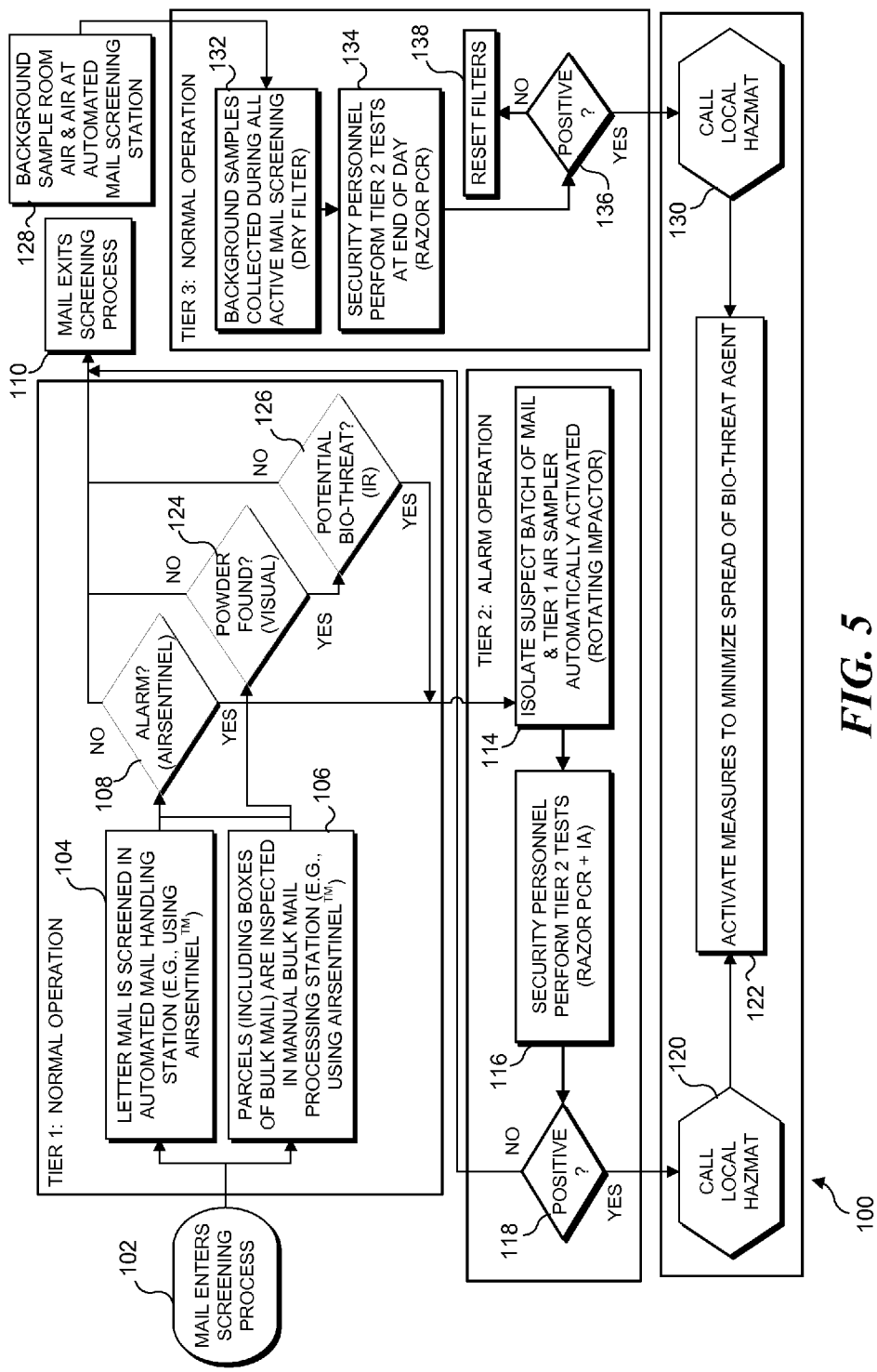

FIG. 3 is a plan view of an exemplary PCR type detector useful in the present approach for providing positive confirmation of any bio-threat detected by the automatic air sampler device of FIG. 2, and for processing samples taken from continuous air samplers installed at automatic and manual mail screening stations, and in the air handling system for the mail room in which mail is being screened for bio-threats, to detect background levels of specific bio-threats;

FIG. 4 is a schematic block diagram illustrating an exemplary procedure used to continuously screen mail to detect possible bio-threats; and FIG. 5 is an exemplary schematic illustration of the process flow employed in one embodiment of the present approach.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Mail Screening in Commercial Mailrooms

A key motivation for employing the USPS solution discussed above under the Background section was that the USPS system has a very low false alarm rate (<1 false alarm/year, which is an extremely low false negative rate—but the initial deployment of the USPS system only scans for anthrax) and a very high probability that anthrax powder (spores) will be detected by the USPS system if present in the mail being screened.

The following describes an alternative novel system that also should achieve these goals, but which is more practical and affordable for use in commercial mailrooms, but also including those of the U.S. Postal Service and government mailrooms. However, it will be understood that the system and method described below is applicable to detecting biothreats in almost any size mailroom or even in other environments where items may be contaminated with bio-threats. This new system also provides a detection capability for a considerably broader range of bio-threat threats. In addition, this new solution specifically addresses the issue of powders found in boxes of bulk mail, large parcels, and generally within the mailroom environment (or in other types of environments). For example, this new solution would be useable by package delivery services, such as UPS, or FedEx, to detect bio-threat contamination of boxes and packages passing through the service. While there is no intent to limit this approach to a mailroom, the following discussion focuses on that initial application in explaining how the multi-tier approach is implemented in a relatively low cost system with extremely good reliability in detecting bio-threats.

Exemplary Bio-Threat Detection System

Mail screening in a commercial setting requires innovative use of hardware appropriate to accomplish the desired goals, combined with a solid concept for operations (CONOPS). In order to reduce cost and minimize contamination of a mailroom by bio-threats, a "detect-to-protect" system is needed that provides a near-real-time detection with, for example, a 1-2 minute response time. This continuous, near-real-time goal will minimize the spread of bio-threats within an environment and the exposure of personnel to contamination by such bio-threats. Costs of such a system can be reduced by carrying out tests that consume assays only after a near-real-time warning sensor has produced an alarm, indicating that a bio-threat may be present, and additionally, at the end of each day (or after some other extended period of time), when checking for background levels of bio-threats at mail screening stations and generally, within the environment of a mailroom.

An exemplary system for detecting bio-threats in mailrooms (referred to herein as the SafeMailRoom™), as described below, should have the following characteristics when the full ensemble of components comprising the system are deployed:

Automatically screens batches of mail at high speed (e.g., 60-180 parcels per minute per machine (i.e., up to about 10,000 parcels/hour)) with integrated rapid detection of bio-threat materials;

Provides an immediate warning to security or other designated personnel when a letter containing more than a normal quantity of a fine powder that is a possible bio-threat is detected and stops the mail screening process to enable that letter or batch of letters to be more completely inspected;

Automatically collects a sample of the powder found during the screening and optionally performs one or more automated microbial screening assays;

Presents the sample for rapid on-site or in situ analysis for several of the most likely biological threats if one or more of the screening assays is positive;

Preserves a sample of the powder for subsequent laboratory analysis, either on site or at a remote laboratory; and Incorporates High Efficiency Particulate Air (HEPA) filtering to protect personnel and the mailroom environment.

Enables manual screening of large parcels and boxes in a safe environment with automated detection of bio-threat materials and integrated HEPA filtering to protect personnel and the mailroom environment; and Provides for immediate on-site testing of any powders and accumulated paper dust to determine if these powders are a potential threat.

In addition, the SafeMailRoom system provider should properly support the hardware with services that includes training for the mailroom personnel in regard to the safe operation of the equipment, including training regarding the appropriate steps to be followed when a positive test is indicated, maintenance and support of the equipment; and steps to be taken to provide for a follow-up laboratory analysis of any powders that test negative, as confirmation that the powders indeed are not a potential threat.

Details of the SafeMailRoom™ System

Figure 1:
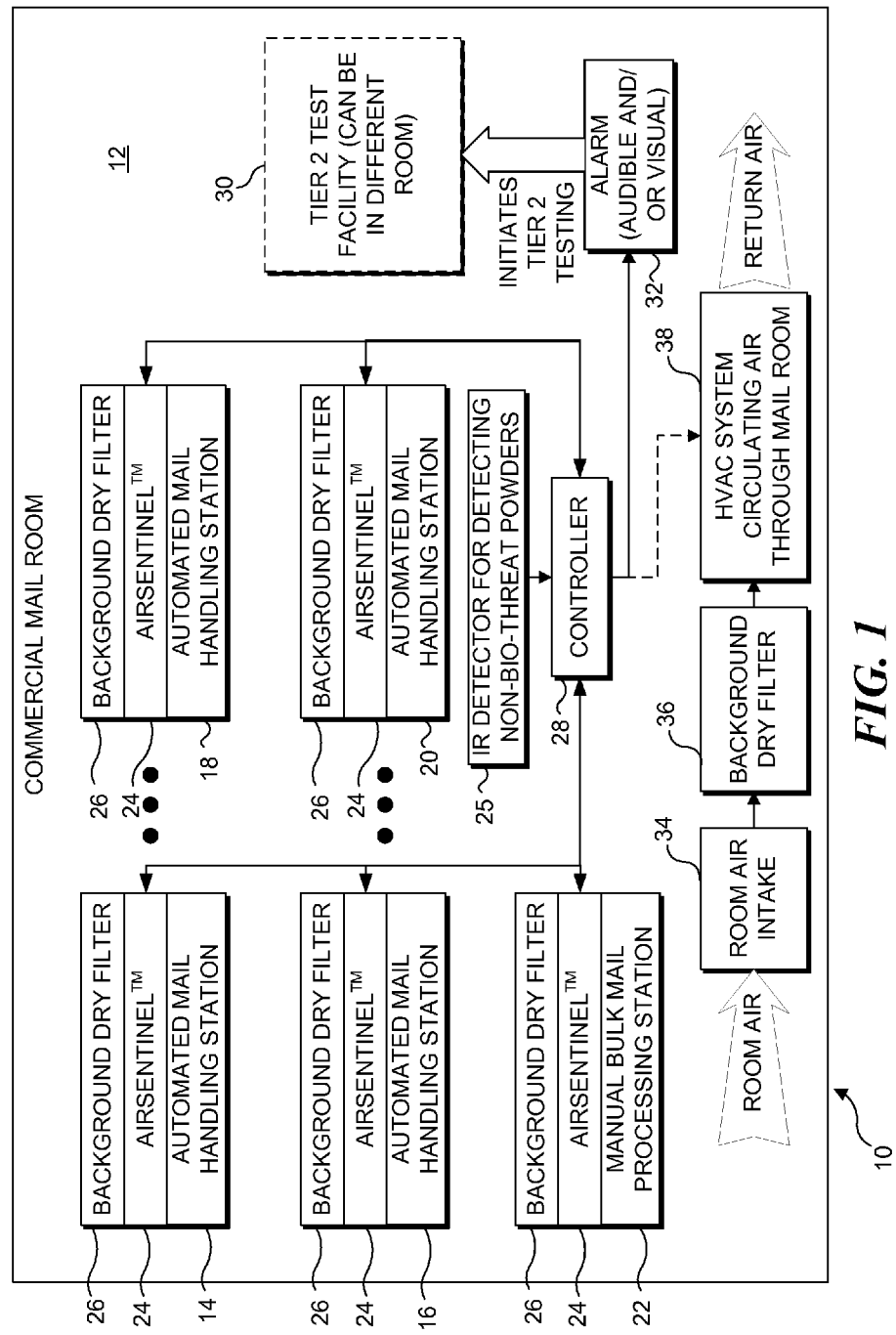
FIG. 1 is a block diagram of an exemplary commercial mail room in which the approach described below is implemented.

The SafeMailRoom™ system addresses all the above requirements with a two-part mail screening system operated on three tiers. The system is designed to work with one or more high-speed mail handling stations 14, 16, 18, and 20, and optionally, with one or more manual bulk mail (and package) processing stations 22, shown in schematic block form in an exemplary large corporate or commercial mailroom 10 in FIG. 1. It is not intended that the number of automated high-speed mail handling stations be limited to the number shown in FIG. 1, since the SafeMailRoom™ system can work with only a manual mail processing station, or with many more automated high-speed mail handling stations than shown in this Figure. Also, in some applications, it is recognized that there may be no need for a manual bulk mail (and package) processing station, or alternatively, a need for many more such stations. The SafeMailRoom™ system can be readily scaled to work with almost any number of automated and/or manual handling or processing stations.

Letter handling in a typical larger mailroom is typically carried out using one or more automated mail sorting and handling machines, like any of automated mail handling stations 14, 16, 18, and 20. Each of these machines can be readily adapted to include a blower (not separately shown) to draw air into the sorter from a vicinity around a tray of mail, and through a HEPA filter (not shown), thereby reducing the quantity of paper dust (and if present, bio-threat materials) in an operating environment 12. The use of such a HEPA filtering system clearly reduces the exposure of personnel to mailroom particulates and aerosols and the associated health risk.

The machine has been further adapted to allow the air surrounding a "pinch point" to be sampled by an aerosol collector. The "pinch point" is a location where each parcel of mail (e.g., a letter) is squeezed between a belt and a pin roller as it is being transported though the machine. The aerosol sample is then continuously routed to a detector for near-real-time analysis. In the exemplary system shown in FIG. 1, a MesoSystems Technology, Inc. AirSentinel® monitor 24 is employed as the detector at each automated handling station and at the optional manual mail processing station. However, it will be understood that other types of continuous monitors that can detect a potential bio-threat might instead be used in the present system. The machine may be further adapted to include a means to perforate the parcels prior to passing through the pinch point, to improve the sensitivity of the detection system.

If an alarm signal is generated by the near-real-time detector, e.g., by AirSentinel® monitor 24, then a signal is transmitted either by a wire or wireless communication signal to a controller 28. In addition, a second sample is collected by the near-real-time detector (or a separate sampler is triggered by said detector) for analysis in a PCR-based agent identification system or by another type of assay component in a second tier of this approach, and the mail handling station is immediately shut down, so that one or more suspect pieces of mail that may be conveying the potential bio-threat substance can be removed and further inspected. Controller 28 can be a conventional personal computer, a hardwired logic device, an application specific integrated circuit (ASIC), or some other computing device or logic device that is configured to carry out specific functions as discussed herein. For example, controller 28 can send a signal by wire or wirelessly to an automated mail handling station where a potential bio-threat was detected by the near-real-time detector, to cause the automated mail handling station to immediately stop processing mail, so that one or more pieces of mail in the batch being processed when the potential bio-threat was detected can be removed for further inspection and evaluation. Other appropriate steps can be initiated to prevent the spread of contamination of the environment, or of personnel, by the possible bio-threat agent. For example, additional filtration of the mailroom air could be implemented.

In addition, controller 28 can respond to the detection of a potential bio-threat by causing an audible or visual alarm 32 to be activated within mailroom 10, and to send a page message or other type of message by wire or wirelessly, to initiate a second tier response autonomously if such equipment is installed, or by summoning trained personnel, to carry out further testing of the sample that was collected by the near-real-time detector, e.g., by AirSentinel™ monitor 24. This second tier testing can be done manually with a device at a facility 30, which can be in mailroom 10 or at a different location to confirm that a bio-threat has actually been detected and if so, to identify a specific bio-threat agent included in the sample. The device used for this second tier determination can be a portable device, such as Idaho Technology Inc.'s Razor™ bio-agent identification system, which employs PCR technology to identify a number of different specific bio-threat agents based upon the DNA of such samples, providing results in about 20-30 minutes. Immunoassay or microbial or protein stain tests can also be used to test for specific bio-threat agents or specific classes of bio-threats, such as anthrax, ricin and botulinum toxin. A portion of the sample can be sent to a laboratory for final confirmation of any specific bio-threat agent identified or to confirm the absence of such a bio-threat.

A special laminar flow hood (not shown) can be used to safely inspect any suspect letters, parcels, or packages, and to enable samples of possible bio-threat particles or powders to be taken from these one or more pieces of mail and sent out for subsequent laboratory analysis that can provide final confirmation of any determination made by the present SafeMailRoom™ system.

A second piece of equipment is needed to compliment the automated mail handling station in many mailrooms. Manual mail opening and screening can be used for suspect mail, odd-sized parcels, boxes of mail, and in small commercial mailrooms where an automated mail screener is not warranted. This task can be carried out at optional manual mail processing station 22. The manual mail processing station can contain a down-draft air flow, a detector such as AirSentinel 24, and a HEPA filter. A Plexiglas air shroud (not shown in the Figure) can be employed to help contain aerosols generated during the opening of parcels, or bulk mail packages.

An infrared (IR) or RAMAN spectrometer 25 can be installed or pre-positioned at each automated mail handling station 14, 16, 18, and 20, and at each manual bulk mail processing station 22, or alternatively, at a single location, to determine whether a potential bio-threat may instead be a non-bio-threat, such as cornstarch powder, artificial sweetener, or talc powder. A potential bio-threat may be visually detected as a powder on mail, and the IR detector then used to determine if the powder is indeed a potential bio-threat.

Each automated mail handling station 14, 16, 18, and 20, and each bulk mail processing station 22 included in mailroom 10 is also fitted with a continuous background air sampler 26 that continuously collects particulates from the air drawn from the vicinity of the mail passing through and being screened at the station. At the end of the day, or at some other predefined period interval of time, these background air samples can be tested to determine whether a lower concentration of bio-threat substances has been collected over time at the station where the background air sampler was installed. The detection of a background bio-threat will not result in an immediate alarm, but serves as a third tier of detection to minimize the risk that lower concentrations of a bio-threat agent being carried by the mail will not be detected by the near-real-time detection system. An exemplary background air sampler is a dry filter sampler, such as the manufactured by Murtech, Inc.

It is also important to detect background levels of a bio-threat agent that are dispersed within environment 12 of mailroom 10. To temperature condition the air within mailroom 10, a heating ventilation air conditioning (HVAC) system 38 draws room air through one or more room air intakes 34. Any potential bio-threat particles that have been picked up and carried by the room air are collected over time on a background air sampler 36 before being drawn into the HVAC evaporator or heating coil temperature conditioning components and exhausted back into environment 12 as temperature conditioned return air. At predefined time intervals, such as at the end of each work shift in mailroom 10, background air sampler 36 can be extracted and particulates collected can be checked to identify any potential bio-threat agents comprising the particles filtered from the room air. This check is another part of the third tier of detection of a bio-threat attack being promulgated via the mail passing through mailroom 10. If a potential bio-threat is detected in the background sample removed from background air sampler 26 at the mail handling or processing stations, or in the background sample removed from the air handling system for mailroom 10 (i.e., background air sampler 36), the detection will be confirmed and if so, the specific bio-threat agent can be identified by summoning the trained personnel to implement the second tier evaluation of the background sample. Once again, an exemplary background air sampler is a dry filter sampler, such as the manufactured by Murtech, Inc.

Bio-Detection Technology

The SafeMailRoom™ system thus relies on three layers, or tiers, of processing and technology to provide a level of redundancy that achieves both a continuous monitoring on the first tier, and which confirms any potential bio-threat threat that is detected in a timely manner in the second tier. A "detect to warn" rapid threat capability is backed up with a "detect to treat" capability, which is also implemented in regard to the third tier after evaluating samples taken over a period of time. This approach leads to a system that has a high probability of detecting large events in near-real-time, but still is able to provide delayed detection of low-level threats.

The table below highlights and summarizes the technologies and objectives of each tier.

| Tier | Technological Approaches | Objectives |
|---|---|---|
| 1 | Ultraviolet light-induced fluorescence (UV-LIF), including fluorescence enhanced with microbial, nucleic acid or protein stains | Discriminate bio-threat particles from paper dust, corn starch, and other non-threat particles |
|  | Particle counts/size/shape | Additional information to support decision on threat vs. non-threat particle clouds |
|  | Rotating impactor air sampler | Collects a sample when the UV-LIF or particle counter detects a possible threat event. |
|  | (Infrared) IR or RAMAN Spectrometer | Specifically identify non-biological powders such as starch, Equal ™ sweetener and talc, indicates when a bio-threat threat may be present. |
| 2 | Nucleic acid amplication and detection (e.g., PCR) | Specifically identifies bio-threat agents. |
|  | Immunoassay tests | Test for specific toxins such as ricin and botulinum toxin to support nucleic acid assays |
|  | Microbial, nucleic acid or protein stains (to be used in conjunction with other Tier 2 tests) | Confirm unknown sample is of biological origin |
| 3 | Background air sampler (e.g., dry filter sampler) | Continuously collects a background sample from mailroom and/or from each mail processing station during all mailroom operations to enable detection of small releases not detected by Tier 1 alarms |
|  | Nucleic acid amplication and detection (e.g., PCR) | Tests background air samples for bio-threat agents. |

Tier 1 Alarm Technology

As noted above, in one exemplary embodiment, the first tier of detection uses AirSentinel™ monitor 24, which contains both a particle counter/sizer and a sensor based on ultraviolet-light-induced fluorescence (UV-LIF). The AirSentinel™ monitor, developed by MesoSystems Technology, Inc. for continuously monitoring indoor air, is readily adapted for use in the mail screening environment and easily fitted to either conventional automated mail handling stations or to manual bulk mail processing stations. However, other types of continuous monitoring devices might instead be used for the real-near-time detector employed for screening mail passing through the automated mail handling stations and any manual bulk mail processing station.

Fluorescence from biological materials is generally distinct from that of other materials, and in particular, from corn starch. For example, the fluorescence is yellow-green from Bacillus spores (including anthrax spores) and bluish-red from corn starch. The AirSentinel™ monitor incorporates color filters on the photodetectors included within it, to enable it to distinguish bio-aerosols from corn starch aerosol. However, paper dust often contains a high concentration of inks and paper dyes, and these materials can interfere with the bio-threat detection. For this reason, alternatives to bulk fluorescence may be useful. The AirSentinel™ monitor includes a particle counter/sizer that can determine a continuous count of particles being drawn in with air from the mail being screened within pre-determined size ranges. The particle count over a pre-determined window of time (hereafter referred to as the "count" or the "count rate") within these predetermined ranges provide additional information that enable potential bio-threat agents to be detected. Typically, letters that do not contain fine powders will produce count rates that are less than 10,000 particles per second in the 0.5-10 micron size range. If an envelope contains loose powder, count rates may be several times higher. The fluorescence signal from a bio-threat material can be enhanced relative to the fluorescence associated with paper dust by contacting the particles with a liquid or gel (or mixing them with a liquid aerosol) that contains stains which fluoresce strongly when bound to nucleic acids or proteins. An impactor or an impinger may be used to contact the particles with a liquid or a gel. Those of ordinary skill in the art will recognize that empirical testing on contaminated and non-contaminated items of mail can be performed to determine exemplary particle count/particle size parameters.

In addition to the UV-LIF detector included in the AirSentinel™ monitor, an IR or RAMAN spectrometer 25 can be used to identify suspect powders that are found anywhere in the mailroom, or specifically in boxes of bulk mail. The IR or RAMAN spectrometer can quickly identify powders such as corn starch. But if the powder is biological in nature, such as bacterial spores or bio-threats, the IR or RAMAN spectrometer can quickly determine that the powder is a potential threat material. In this situation, a Tier 2 biological detection assay is required to confirm the detection and if confirmed, to identify a specific type of bio-threat agent present in the powder.

Tier 1 Sampling Technology

AirSentinel™ monitor 24 which is shown in FIG. 2, has an integrated air sampler, which is based on MesoSystems' proprietary rotating impactor technology. The AirSentinel™ monitor draws air through a sensor inlet 40, to initially determine if the air is conveying a potential bio-threat agent, and if a potential bio-threat agent is detected, air conveying the potential bio-threat agent is then drawn through a sample inlet 42 to create a sample of the potential bio-threat agent on a substrate disk (not visible in this Figure) for use in carrying out further testing in the Tier 2 procedure, and for use in carrying out any further final confirmation of the Tier 2 results in a clinical laboratory. It should be recognized that Tier 1 sampling functions as a trigger, such that once Tier 1 indicates that a potentially harmful agent might be present, additional sampling and analysis is performed in Tier 2 to verify that a harmful agent actually is present, and to attempt to specifically identify the harmful agent.

FIG. 4 includes a schematic block diagram 70 that illustrates some of the functions performed within the AirSentinel™ monitor to detect a potential bio-threat and then, to collect a sample for further analysis. Air carrying particles 74 is drawn through sample inlet 42 (FIG. 2) and pulled through an air impactor (not shown), exiting through a port 72 for deposition as a spot or sample 78, on a sample plate 76, as shown in FIG. 4. Exhaust air exits through an outlet port 80. Particles deposited as spot or sample 78 are irradiated with an ultraviolet light 82, which is focused by a lens 84. Any fluorescent light 86 emitted by the particles comprising spot or sample 78 is focused by another lens 88 onto a fluorescent light detector (not shown), which produces a corresponding fluorescent signature signal (for example, indicative of the wavelength of the fluorescent light). Based upon the fluorescent signature signal produced by the detector, the logic in the AirSentinel monitor (or other near-real-time detector) is used in a decision step 90 to determine if there appear to be elevated biological levels corresponding to a potential bio-threat by the particles of the sample just collected on sample plate 76. (In addition, the particle count and particle size can be employed in making this determination.) If not, sample plate 76 is cleaned in a step 96 to substantially remove the last spot or sample of particles, in preparation for receiving the next spot or sample.

However, if it appears that the particles include a potential bio-threat agent, a secondary sample is collected on a sample plate 92, which can be retrieved for processing in the Tier 2 procedure by trained personnel and optionally, for subsequent final confirmation of the result of that Tier 2 processing by a clinical laboratory, as indicated in block 94. In addition, an alarm signal is produced that is used to initiate Tier 2, by summoning the trained personnel who will be carrying out further testing of the secondary sample collected on sample plate 92. Also, the alarm signal can be employed to stop the automated or manual processing of mail by the station on which the potential bio-threat agent was detected, alert personnel of the potential bio-threat hazard with an audio and/or visual alarm, and control air flow through the mail room to prevent possibly contaminated air from being spread outside the mailroom.

Tier 1 is designed to operate autonomously (automatically without manual intervention) and if a letter contains a potentially hazardous powder, it can detect that threat in less than one minute. This rapid response time enables a suspect letter to be isolated for further inspection and removes the risk that the letter will be delivered to the intended recipient, who might then be exposed to the bio-threat agent conveyed by the letter. This capability also reduces the risk of contamination of people and assets in the mail processing and delivery system while keeping all the normal mail moving quickly. It is expected that ordinary (non-hazardous) mail will generate some false alarms periodically, and when that happens, a sample is automatically collected for a Tier 2 analysis, which should quickly determine that the alarm was not justified. Conversely, the Tier 2 analysis can quickly confirm that a real bio-threat agent has been detected by the Tier 1 procedure and then identify the specific bio-threat agent that has been found.

Tier 2 Bio-Detection Technology

The heart of the Tier 2 detection technology in one exemplary embodiment of the SafeMailRoom™ system is a Razor™ bio-agent identification system 50, which is shown in FIG. 3. The Razor incorporates the state-of-the-art PCR "DNA fingerprint" technology currently deployed by the USPS system. The Razor™ device does not operate continuously, but, when the Tier 1 sensor in AirSentinel™ monitor 24 detects a potential bio-threat agent, and in response, generates an alarm signal and collects a sample, that sample is first prepared for analysis by a trained technician, and then injected into the Razor™ device. The results of the test are available about 20-30 minutes later. The sample preparation takes about 10 minutes, so a complete Tier 2 test takes approximately 30-40 minutes. The Razor™ system is capable of detecting a very small quantity of a bio-threat agent—i.e., much less than a microgram of powder. It is also very specific in that it identifies specific threat organisms from among a plurality of different types of bio-threat agents and it is not prone to false positives or false negatives.

The Razor™ system shown in FIG. 3 includes a power switch 52, as well as a plurality of other control buttons 54 on the top panel of the device, disposed around a display screen 56 that displays different messages and indicates the status of the device as it performs different processing functions. Also included on the top of the device are a cover lock 58, which secures a hinged cover 64 (shown in the open position), an external power port 60 (the Razor™ is portable and normally battery operated), and an RS-232 serial data port 62. A plurality of thin-film sample pouches 66 are used as reaction containers for the PCR assay tests that are performed by the Razor™ device.

The drawbacks of Tier 2 are that it does not provide an immediate response and these technologies do not operate autonomously. A trained technician is normally required to perform these tests, although as the technology matures, the tests become more automated and require less training. However, Tier 2 does provide an unambiguous test result that is not subject to false alarms, and it does so within 30 minutes from when a Tier 1 alarm is generated. Because the Tier 2 tests can be completed in 30 minutes, large amounts of storage area are not required to quarantine mail while laboratory tests are being completed off-site.

Immunoassay tests and other commercial nucleic acid and protein stain-based tests can be used in connection with PCR, or other genetic fingerprinting assays, as components of Tier 2. Mass spectrometers may all also provide an alternative fingerprinting technology suitable for Tier 2.

Tier 3 Bio-Detection Technology

While Tier 1 and Tier 2 combine to provide an early warning system, the third tier might be viewed as the "last line of defense." The third tier consists of background air sampler 26 attached to each mail handling station for sampling the air passing over the mail being screened at the station, and background air sampler 36 attached to the air handling system and sampling the room air. At the end of each day, samples of the particulates on the background air samplers are collected, aggregated, and then tested using the Razor™ device, or some other type of manual system, for identifying specific bio-threat agents.

The purpose of Tier 3 is provide a "detect-to-treat" capability similar to the USPS, should the Tier 1 system fail to produce an alarm in near-real-time for any reason when a threat is present in a parcel. For relatively low concentrations of a bio-threat agent present on the mail, the background air sampler can collect sufficient amounts of the agent over time, to be more readily detected and identified.

The CONOPS (Concept for Operations) Approach

During normal operations, bulk mail enters the mailroom and is screened for bio-threats. The screening operation takes place in either the Automated Mail Screening Station or the Manual Mail Inspection Station. If no alarms are generated, which will normally be the case, the mail is processed and distributed as normal.

If an alarm is generated, then the batch of mail that generated the alarm is quarantined and Tier 2 testing is initiated. A pager signal is generated to alert building security of the alarm. Tier 2 testing is performed by trained security personnel using portable equipment that they bring to the mailroom. These operations are shown schematically in a block diagram 100 in FIG. 5. The Figure not only shows the flow of mail as it is screened, but also the decision process as alarms are generated or powders are found by visual inspection, in the mail. The Figure also shows where the technology is utilized.

Mail enters the Tier 1 screening process at a block 102. Most of the mail will likely be screened in the automated mail handling stations, for example, using the AirSentinel® monitor, as indicated in a step 104. Parcels such as boxes or bulk mail can be inspected at a manual bulk mail processing station, as noted in a step 106. If the continuous near-real-time detector, such as the AirSentinel® monitor does not detect a potential bio-threat in a decision step 108, the process enables the mail to exit the screening process in a step 110. Similarly, if a visual inspection does not find a powder on a parcel or package at the manual bulk mail processing station, the bulk mail being that has passed this initial screening is enabled to exit the screening process at step 110. However, if the continuous near-real-time detector, such as AirSentinel® monitor 24 detects a potential bio-threat, an alarm signal is produced that leads to a step 114 in the Tier 2 procedure. Step 114 provides for isolating the batch of mail that includes one or more pieces that may have conveyed the potential bio-threat agent. In addition, this step provides for automatically collecting a secondary sample using the rotating impactor, as discussed above. At a step 116, trained security personnel perform the Tier 2 tests of the sample collected by the near-real-time detector (e.g., the AirSentinel® monitor) to confirm whether the potential bio-threat agent is actually a bio-threat and if so, to identify the specific bio-threat agent. If the potential bio-threat agent is found to be a harmless substance, such as talc or cornstarch in a decision step 118, the mail involved in the Tier 2 evaluation is allowed to exit the screening process at step 110. Conversely, if the alarm is confirmed and specific bio-threat agent is identified by the Tier 2 tests, the local hazmat team is immediately called in a step 120. Mail processing operations are immediately stopped in the mailroom, and personnel are required to stay in the mailroom to avoid the potential for spread of the bio-threat contaminant. Control of the mailroom is yielded to the incident commander on the hazmat team as soon as the hazmat team arrives. It is quite possible that a positive test will never occur since real bio-terror events are rare, and false positives from the second and third tiers are virtually non-existent, due to the high specificity of PCR for identifying specific bio-threat agents.

With reference to decision step 124, if a powder is visually found on a package or other bulk mail at a manual bulk mail processing station, a decision step 126 determines if the powder is a potential bio-threat, for example, by accessing the IR characteristics of the powder. If the characteristics indicate that the powder is a potential bio-threat, an alarm is sounded, and the powder is provided as a sample for Tier 2 processing at step 114, as discussed above. Conversely, if it appears that the powder is not a bio-threat, then the bulk mail or parcel is enabled to exit the screening process at step 110.

Tier 3 testing is performed by security personnel after the mailroom operations have ended for the day. A step 128 indicates that the system samples air at each automated mail handling and manual bulk mail processing station over a period of time. In a step 132, background samples taken by the background air samplers at each station and in the air handling system are collected. In a step 134, trained security personnel perform the Tier 2 tests, for example, using the Razor™ device to carry out PCR testing of the samples. After the Tier 3 test is completed, the background air samplers are recharged if necessary in a step 138, and the mailroom is set for normal operations in the morning or following time period of operation. If a Tier 3 test returns a positive by identifying a specific bio-threat in any of the background samples in a decision step 136, the local hazmat team is immediately notified in step 130 and the procedures associated with a Tier 2 positive test are followed, as in step 122.

Support services that are an integral part of the SafeMail-Room™ system include:

Training for the mailroom personnel on safe operation of the equipment, including for when a positive test is indicated;

Maintenance and support for the equipment; and

Follow-up laboratory analysis on any powders that test negative.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention claimed is:

1. A method for screening mail to detect a harmful substance conveyed by the mail; comprising steps of:
    (a) automatically sampling air drawn from the vicinity of the mail to screen wherein the sampling comprises continuously sampling the air proximate each one of a plurality of mail handling stations, and further comprising the steps of:
        (i) deploying a filter unit through which air proximate each one of the plurality of mail handling stations is filtered; and
        (ii) at the end of a predetermined period of time, analyzing particles collected by each filter unit, in order determine if relatively low concentrations of potentially harmful particles were missed by the automatic evaluation of the air sampled at the mail handling station, such relatively low concentrations accumulating over the predetermined period of time into a detectable concentration in the filter;
    (b) automatically evaluating the sampled air to detect a potentially harmful substance that is carried by the mail and which is picked up from the mail by the air moving in the vicinity of the mail, such evaluation being characterized as broadly determining if a potentially harmful substance must be present, as opposed to identifying a specific harmful substance, the evaluation comprising:
        (i) determining if a particle count is the sample exceeds a predetermined threshold, and if so determining that a potentially harmful substance might be present; and
        (ii) illuminating the sample to determine if a characteristic fluorescence indicating the presence of biological particles is detected, and if so, determining that a potentially harmful substance might be present;
    (c) providing and indication if a potentially harmful substance is detected while the mail is being screened; and
    (d) in response to the indication of a potentially harmful substance being detected, carrying out an assay of a sample of the potentially harmful substance, to confirm the indication and to attempt to identify a specific harmful substance that is being conveyed by mail.

2. The method of claim 1, wherein the step of carrying out the assay of the sample comprises:
    the step of using a portable analytical device to perform the assay, such that a sample does not need to be removed from an area where the mail is disposed for analysis.

3. The method of claim 1, wherein if the assay either confirms the indication or identifies a specific harmful substance, then automatically initiating an appropriate response, to minimize one of more of:
    (a) exposure to personnel to the specific harmful substance;
    (b) further contamination of an environment where the mail is disposed, by specific harmful substance; and
    (c) spread of the specific harmful substance outside of said environment.

4. The method of claim 3, wherein the step of initiating the appropriate response comprises at least one step selected from the group of steps consisting of:
    (a) stopping all further processing of mail in each room where the mail carrying the specific harmful substance had been disposed;
    (b) informing hazmat personnel who are trained in responding to handling contamination mail that a specific harmful substance has been identified in the mail, to enable the hazmat personnel to carry out other predefined steps to contain a contamination by the specific harmful substance;

(c) preventing any personnel from leaving each room where the mail carrying the specific harmful substance had been disposed; and (d) controlling air circulation systems to prevent air that may be contaminated with the specific harmful substance from being circulated into rooms that may not yet be contaminated.

5. The method of claim 1, wherein the potentially harmful substance included at least one substance selected from the group consisting of:

(a) bacterial spores;

(b) bacteria;

(c) viruses; and (d) toxins derived from organisms, either living or once living.

6. The method of claim 1, wherein the step of carrying out the assay of the sample comprises at least one of the steps selected from the group consisting of;

(a) performing a stain-based assay to determine if the sample includes an unusually high number of particles of biological origin;

(b) performing a polymerase chain reaction (PCR) amplification and detection assay of the potentially harmful substance configured to identify the presence of a genetic fingerprint of at least one specific harmful substance;

(c) performing an immunoassay test to detect the presence of the potentially harmful substance, where the immunoassay test is selected to identify at least one specific harmful substance; and (d) performing a nucleic acid assay to identify the presence of the genetic fingerprint of at least one specific harmful substance.

7. The method of claim 1, further comprising the step of periodically carrying out an assay to detect a background level of a specific harmful substance within an environment where the mail has been disposed.

8. The method of claim 7, wherein the step of carrying out the assay to detect the background level of a specific harmful substance within the environment comprises at least one of the steps selected from the group consisting of:

(a) performing a nucleic acid amplification and detection assay test of a sample collected from air moving through the environment, wherein the nucleic acid amplification and detection assay test is configured to identify at least one specific harmful substance; and (b) exposing an immunoassay test to the potentially harmful substance, where the immunoassay test is selected to identify at least on specific harmful substance when exposed to the sample collected from air moving through the environment.

9. The method of claim 1, further comprising the step of periodically carrying out an assay of a sample collected from air passing through each station where the mail has been screened, to detect a background level of a specific harmful substance collected from the air over time.

10. The method claim 9, wherein the step of carrying out the assay to detect the background level of a specific harmful substance in a sample collected over time from air passing through each station comprises at least one of the steps selected from the group consisting of:

(a) performing a nucleic acid amplification and detection assay test of the sample collected from the air passing through the station, wherein the nucleic acid amplification and detection assay test is configured to identify at least on specific harmful substance; and (b) exposing an immunoassay test to sample, where the immunoassay test is selected to identify at least one specific harmful substance when exposed to the sample collected from air passing through the station.

11. The method of claim 1, wherein in response to the indication of a potentially harmful substance being detected, further comprising the steps of:

(a) producing an alarm signal that is perceptible by personnel in the environment where the mail is being screened;

(b) quarantining the mail that is carrying the potentially harmful substance; and (c) collecting the sample of the potentially harmful substance for use in carrying out the assay.

12. The method of claim 1, wherein the step of illuminating the sample to determine if a characteristic fluorescence indicating the presence of biological particles is detected comprises of the steps of:

(a) depositing particles from the air sampled onto a substrate;

(b) directing light of an appropriate wavelength onto the deposited particles;

(c) determining if the characteristic fluorescence is present; and (d) automatically cleaning the substrate such that new particles can be deposited and illuminated.

13. A method for screening mail to detect a harmful substance conveyed by the mail, comprising the steps of;

(a) automatically sampling air drawn from a vicinity of the mail to screen the mail;

(b) automatically evaluating the sampled air to detect a potentially harmful substance that is carried by the mail and which is picked from the mail by the air moving in the vicinity of the mail, such evaluation being characterized as broadly determining if a potentially harmful substance might be present, as opposed to identifying a specific harmful substance, the evaluation comprising:

(i) determining if a particle count in the sample exceeds a predetermined threshold, and if so determining that a potentially harmful substance might be present; and (ii) illuminating the sample to determine if a characteristic fluorescence indicating the presence of biological particles is detected, and if so, determining that a potentially harmful substance might be present:

(c) providing an indication if a potentially harmful substance is detected while the mail is being screened;

(d) in response to the indication of a potentially harmful substance being detected, carrying out an assay of a sample of the potentially harmful substance, to confirm the indication and to attempt to identify a specific harmful substance that is being conveyed by the mail; and (e) visually inspecting parcels or boxes of mail to detect a powder that may comprise a potentially harmful substance; and (f) if a power that may comprise a potentially harmful substance is visually detected during the step of visually inspecting, then using a portable infrared Raman spectrometer to attempt to identify the powder, and if the powder cannot be identified using the portable infrared Raman spectrometer, carrying out an assay of the powder, to attempt to identify a specific harmful substance comprising the powder, the assay comprising at least one of the following:

(i) a nucleic acid amplification and detecting assay test; and (ii) an immunoassay test.

* * * * *